(12) United States Patent
Barney et al.

(10) Patent No.: US 7,105,177 B1
(45) Date of Patent: Sep. 12, 2006

(54) ANTIMICROBIAL DIAPERS AND WET WIPES

(75) Inventors: Michael C. Barney, Elm Grove, WI (US); Alfonso Navarro, Milwaukee, WI (US); David S. Ryder, Mequon, WI (US)

(73) Assignee: Miller Brewing Company, Milwaukee, WI (US)

( * ) Notice: Subject to any disclaimer, the term of this patent is extended or adjusted under 35 U.S.C. 154(b) by 0 days.

(21) Appl. No.: 09/693,123

(22) Filed: Oct. 20, 2000

(51) Int. Cl.
*A61F 13/00* (2006.01)
*A61L 15/00* (2006.01)
*A61L 15/16* (2006.01)
*A01N 25/34* (2006.01)

(52) U.S. Cl. .................. 424/443; 424/445; 424/446; 424/447; 424/449; 424/402

(58) Field of Classification Search ......... 424/402, 424/430, 431, 443, 449, 445, 446, 447; 514/689; 604/360
See application file for complete search history.

(56) References Cited

U.S. PATENT DOCUMENTS

| | | | |
|---|---|---|---|
| 4,405,323 A | 9/1983 | Auerbach | 604/285 |
| 4,408,996 A | 10/1983 | Baldwin | 8/490 |
| 4,431,427 A | 2/1984 | Lefren et al. | 604/285 |
| 4,644,084 A | 2/1987 | Cowles et al. | 568/341 |
| 5,071,648 A | 12/1991 | Rosenblatt | |
| 5,082,975 A * | 1/1992 | Todd, Jr. et al. | |
| 5,166,449 A | 11/1992 | Todd, Jr. et al. | 568/377 |
| 5,389,374 A | 2/1995 | Brown-Skrobot | |
| 5,455,038 A | 10/1995 | Barney et al. | 424/405 |
| 5,592,949 A * | 1/1997 | Moench et al. | 128/837 |
| 5,753,252 A * | 5/1998 | Brown-Skrobot | |
| 5,827,895 A | 10/1998 | Nutter et al. | 514/690 |
| 5,840,760 A * | 11/1998 | Carraher, Jr. et al. | |
| 6,183,763 B1* | 2/2001 | Beerse et al. | 424/404 |
| 6,262,038 B1* | 7/2001 | Pierce et al. | |
| 6,284,261 B1* | 9/2001 | Tramontana | |
| 6,313,178 B1* | 11/2001 | Nutter et al. | |
| 6,548,552 B1* | 4/2003 | Deresiewicz et al. | 514/706 |
| 6,706,276 B1* | 3/2004 | Garg et al. | 424/433 |

FOREIGN PATENT DOCUMENTS

| | | |
|---|---|---|
| EP | 606599 A1 | 7/1994 |
| WO | WO 98/11883 A1 | 3/1998 |
| WO | WO 00/61201 A1 | 10/2000 |
| WO | WO 01/26647 A1 | 4/2001 |

OTHER PUBLICATIONS

PCT Search Report for PCT/US01/50963.

* cited by examiner

*Primary Examiner*—Isis Ghali
(74) *Attorney, Agent, or Firm*—Quarles & Brady LLP

(57) ABSTRACT

Diapers and wet wipes for cleansing of infants are made anti-bacterial by the inclusion therein of hop acid derivatives, specifically tetrahydroiso-alpha acid and hexahydro-beta acid. These compounds are effective to inhibit the growth of gram-positive bacteria, and specifically chosen to combat *Staphylococcus aureus*, a primary factor in toxic shock syndrome in infants.

4 Claims, No Drawings

ANTIMICROBIAL DIAPERS AND WET WIPES

CROSS REFERENCES TO RELATED APPLICATIONS

Not applicable.

STATEMENT REGARDING FEDERALLY SPONSORED RESEARCH

Not applicable.

BACKGROUND OF THE INVENTION

This invention relates to the application of specific antimicrobial agents to diapers and wet wipes for the protection of infants from strains of the bacterium *Staphylococcus aureus*, which is known to be a causative agent of toxic shock syndrome (TSS). Toxic shock syndrome is a severe, toxin-induced disease caused by infection with toxic shock syndrome toxin-1 (TSST-1) (Iandolo, *Ann. Rev. of Micro.* 43:275–402, 1989) which is produced by *Staphylococcus aureus*, and is characterized by sudden onset of symptoms including high fever, chills, rash, vomiting and/or diarrhea, and a rapid drop in blood pressure, which often leads to shock. While most commonly seen in menstruating women, in whom the primary site of infection is vaginal, the syndrome has also been reported in infants, children, men, and nonmenstruating women at a lower frequency rate. In such cases, skin wounds or *Staphylococcus aureus* infection in other sites in the body are believed to be the cause of TSS. The rate of incidence of the syndrome in the United States is about two cases per 10,000 persons annually.

While the disease may be treated with antibiotics and by administration of intravenous fluids to maintain blood pressure, many persons suffering from toxic shock syndrome may not receive appropriate medical intervention before serious complications result, due to the sudden onset of the syndrome. This is particularly true in the case of infants and children. Typically, such complications may include kidney failure, heart failure, liver failure, and profound shock.

Because TSS has such a rapid onset, and may be life-threatening, there is a very strong emphasis on disease prevention, with most of the concentration being upon menstruating women, who are at increased risk of developing TSS through the use of highly absorbent tampons or barrier contraceptives. Various approaches to preventing the development of toxic shock syndrome from tampon use have been advanced, including incorporating bactericidal or bacteriostatic agents such as antibiotics or phenol into tampons to inhibit grown of *Staphylococcus aureus*; incorporating agents which prevent the production of TSST-1, or inactivate TSST-1; and mechanical improvements to tampons which prevent harmful bacteria from being introduced into or colonizing within the vagina.

A number of U.S. patents have issued relative to this matter, including U.S. Pat. No. 4,405,323, the content of which is incorporated herein by reference, as if fully set forth herein, which discloses a tampon having an antibacterial agent such as povione-iodine, mercury, zinc, penicillin, erythromycin, or nitrofurazone, incorporated therein. U.S. Pat. No. 4,431,427, the content of which is incorporated herein by reference, as if fully set forth herein, discloses a tampon incorporating a water-soluble acid, such as citric, glycolic, malic, tartaric, or lactic acid, in an amount sufficient to maintain a pH of less than 4.5 in the fluids absorbed in a tampon, so as to inhibit growth of pathogenic bacteria.

It is also known that some hop acids produced in the brewing of beer can inhibit the growth of microorganisms. U.S. Pat. No. 5,082,975, the content of which is incorporated herein by reference, as if fully set forth herein, discloses that the hop acid hexahydrolupulone can inhibit the growth of *Lactobacillus* without inhibiting yeast. Similarly, U.S. Pat. No. 5,455,038, the content of which is incorporated herein by reference, as if fully set forth herein, teaches that *Listeria* in a medium or in food may be inhibited by contact with an effective amount of hexahydrocolupulone, tetrahydroisohumulone, or a salt of hexahydrocolupulone or tetrahydroisohumulone. Hop acids are relatively inexpensive, making their use to inhibit growth of organisms attractive. Also, resistance of *Staphylococcus aureus* has not been described as has the resistance to various antibiotics. The term "tetrahydroisohumulone" as used herein includes a mixture of tetrahydroisohumulone, tetrahydroisoadhumulone and tetrahydroisocohumulone. The mixture is commercially available, or can be prepared for example by use of the method of the Cowles et al. U.S. Pat. No. 4,644,084, the content of which is incorporated herein by reference, as if fully set forth herein. The hexahydrocolupulone is a known compound which can be made by the chemical hydrogenation of colupulone with platinum (IV) oxide as the catalyst as described by W. Reidl, J. Nickl, *Ber;* 89 (1956) p. 1863, or J. F. Carson, J. Am. Chem. Soc., 73 (1951) p. 1850.

Further, Nutter et al. disclosed in U.S. Pat. No. 5,827,895, the content of which is incorporated herein by reference, as if fully set forth herein, that hexahydrolupulones and hexahydrocolupulones may be used to inhibit the growth of *Staphylococcus aureus*. Nutter et al. also reported that the antimicrobial activity of hexahydrolupulones is highly specific for gram positive bacteria, such as *Staphylococcus aureus*.

In addition, Todd et al, in U.S. Pat. No. 5,166,449, the content of which is incorporated herein by reference, as if fully set forth herein, note the antibacterial activity of beta acids (lupulone), as a constituent of hops, and methods for their conversion to tetrahydroiso-alpha and hexahydro-beta acids. The patent also teaches the use of such compounds for inhibition of the bacterium *Lactobacillus*.

However, no methods have to date been found to effectively eliminate or inhibit growth of *Staphylococcus aureus*, or toxins produced thereby, in skin wounds or other sites of the body, particularly in infants. Since infants are sensitive to TSS, and infants of diaper wearing age particularly so, a means to prevent TSS associated with infection from skin contact has been sought.

BRIEF SUMMARY OF THE INVENTION

The present invention provides a means for prevention of TSS in infants of diaper wearing age, by provision of diapers and wet wipes for use in cleansing of infants, wherein said diapers and wet wipes contain an antimicrobial compound effective against TSST-1, and thus against TSS. It has now been discovered that certain hop acid derivatives are highly bactericidal to gram positive bacteria, and are particularly effective at killing *Staphylococcus aureus*, the causative agent of toxic shock syndrome, at extremely low concentrations. These derivatives are tetrahydroiso-alpha acids, and/or hexahydro-beta acids, and mixtures thereof. Both of these derivatives have now been found to have greatly enhanced antimicrobial properties compared to the hop acids, humulone and lupulone. The two derivatives may be used independently, or together, with positive effect.

When applied to diapers, particularly disposable diapers, these derivatives essentially eliminate the growth of *Staphylococcus aureus* and toxins associated therewith, including toxic shock syndrome toxin-1, in diapers in contact with the skin. These compositions may also be applied to wet wipes used to clean the infant when changing diapers, and will inhibit *Staphylococcus aureus* on skin surfaces, thus reducing the risk of toxic shock syndrome in infants of diaper wearing age.

It is thus an advantage of the present invention to provide an inexpensive method for inhibiting the occurrence of TSS in infants. It is a further advantage of the present invention to provide a wet wipe suitable for use not only on infants of diaper wearing age, but for use on any skin wound or area of possible infection, which is antimicrobial against Gram-positive bacteria, and particularly against *Staphylococcus aureus*. A still further advantage is that the effective-medium is a naturally occurring derivative of a natural source, and is readily biodegradable as well as being safe for human consumption, in concentrations which will kill *Staphylococcus aureus* as well as other Gram-positive bacteria.

DETAILED DESCRIPTION OF THE INVENTION

Toxic shock syndrome is a serious, potentially fatal illness that occurs with sudden onset, and occurs primarily in menstruating women. However, toxic shock syndrome is also known to effect infants, children, men, and nonmenstruating women, primarily from skin wounds or infection of other sites in the body by *Staphylococcus aureus* and the toxic shock syndrome toxin-1. It has now been found that certain specific hop-acid derivatives, specifically tetrahydroiso-alpha acids and hexahydro-beta acids, will inhibit the growth of *Staphylococcus aureus* and other Gram-positive bacteria when applied topically to a skin wound, or when incorporated in a diaper or other dressing, such as a bandage, in contact with the skin.

Since toxic shock syndrome in infants has been attributed to the growth of *Staphylococcus* on baby diapers, the addition of anti-*Staphylococcus* compounds, specifically tetrahydroiso-alpha acids and hexahydro-beta acids, to materials used in disposable baby diapers as well as to wet wipes used to clean the baby during diaper changes would inhibit *Staphylococcus aureus* and reduce the risk of toxic shock syndrome. Tetrahydroiso-alpha acids and hexahydro-beta acids also inhibit all other Gram-positive bacteria tested, and to a lesser amount some Gram-negative bateria, which may also colonize and grow in disposable baby diapers. Therefore, there would be an added benefit of helping to eliminate bacteria other than *Staphylococcus* that could cause potential infections.

The preferred embodiment of the present invention thus comprises incorporating a safe and effective concentration of tetrahydroiso-alpha acid, hexahydro-beta acid, or mixtures thereof, in the surface layer of a disposable diaper, or in the wetting solution of a wet wipe, to combat the growth of bacteria on infants. By the term "an effective amount of the compound" it is meant that sufficient of the compound is present to provide the desired anti-microbial effect, but not so much as to cause any undesirable result, or to be prohibitively expensive. By the term antimicrobial, it is meant that the composition, at a minimum, inhibits the growth of bacteria, and preferably, destroys such bacteria as are present.

It is known in the brewing industry that some hop acids can inhibit the growth of microorganisms that can cause spoilage in beer. Hop acids are relatively inexpensive, making their use in food products to inhibit growth of organisms attractive. From this recognition came the discovery that tetrahydroiso-alpha acids and hexahydro-beta acids have bactericidal or bacteriostatic activities against *Staphylococcus aureus*. This makes it possible to selectively inhibit *Staphylococcus aureus* in a culture by contacting the culture with a tetrahydroiso-alpha acid or hexahydro-beta acid in a concentration effective to inhibit *Staphylococcus aureus*.

To selectively inhibit *Staphylococcus aureus* in culture by contacting the culture with a tetrahydroiso-alpha acid or hexahydro-beta acid, the concentration of tetrahydroiso-alpha acid or hexahydro-beta acid is preferably in the range of from about 0.1 ppm to about 100 ppm, based upon the total culture. More preferably, the concentration of tetrahydroiso-alpha acid or hexahydro-beta acid is about in the range of from about 0.2 ppm to about 50 ppm of the total culture. Since the hop compounds utilized are relatively stable compounds, they may be used as a solution sprayed on the finished diapers, or applied as a liquid during manufacture of the diapers, and subsequently dried. Once the compounds are dried, with sufficient compound remaining in situ to provide an effective amount of the compound on the diaper in use, they are relatively stable.

The preferred mode of contacting the culture comprising *Staphylococcus aureus* with the hop acids is to place an absorbent material containing an effective amount of the hop acids in contact with or in proximity to the culture.

The following non-limiting examples are intended to be purely illustrative.

EXAMPLES

Minimal inhibitory concentration (MIC) assays of several hop compounds were conducted using a *Staphylococcus aureus* species as the test microorganism. The MCI assays for *Staphylococcus aureus* were conducted in Difco trypticase soy broth (TSB) tubes. A 0.1 ml aliquot of a 1% (w/w) solution of each hop acid in alcohol was added to a tube of sterile TSB broth to give a final concentration of 100 ppm of the hop. This solution was serially diluted in tubes with sterile broth using a two-fold dilution series. A second dilution series prepared as above, but using 0.1 ml alcohol without hop acid, was used as a positive control of bacterial growth. Each tube was inoculated with a fresh culture ($10^4$ cells) of a *Staphylococcus aureus* species in TSB broth. The pH of the TSB was adjusted to pH 7.0, pH 6.0, or pH 5.0 using hydrochloric acid. The tubes were incubated aerobically at 37° C. for three days and growth was evaluated by visually assessing and scoring the development of turbidity in the broth.

The results of MIC assay of tetrahydroiso-alpha acids and hexahydro-beta acids on *Staphylococcus aureus* and are shown in Table 1.

As can be seen from Table 1, *Staphylococcus aureus* is very sensitive to both tetrahydroiso-alpha acids and hexahydro-beta acids. *Staphylococcus aureus* showed no growth or possibly very weak growth at tetrahydroiso-alpha acid or hexahydro-beta acid concentrations as low as 1.56 ppm at a neutral pH. Sensitivity of *Staphylococcus aureus* appears to increase under acidic conditions, with the minimum inhibitory concentration decreasing to 0.78 ppm at pH 6.0 and to 0.2 ppm at pH 5.0.

TABLE 1

MIC Assays of Tetrahydroiso-alpha Acids and
Hexahydro-beta Acids using *Staphylococcus aureus*

| concentra- | TSB at pH 7.0 | | TSB at pH 6.0 | | TSB at pH 5.0 | |
|---|---|---|---|---|---|---|
| tion (ppm) | Tetra | Hexa | Tetra | Hexa | Tetra | Hexa |
| 100 | No growth | No growth | No growth | No growth | No growth | No growth |
| 50 | No growth | No growth | No growth | No growth | No growth | No growth |
| 25 | No growth | No growth | No growth | No growth | No growth | No growth |
| 12.5 | No growth | No growth | No growth | No growth | No growth | No growth |
| 6.25 | No growth | No growth | No growth | No growth | No growth | No growth |
| 3.125 | No growth | No growth | No growth | No growth | No growth | No growth |
| 1.56 | +/− Growth | +/− Growth | No growth | No growth | No growth | No growth |
| 0.78 | + Growth | + Growth | No growth | No growth | No growth | No growth |
| 0.39 | ++ Growth | ++ Growth | +/− Growth | No growth | No growth | No growth |
| 0.2 | +++ Growth | +++ Growth | ++ Growth | + Growth | No growth | No growth |
| 0 | +++ Growth | +++ Growth | +++ Growth | +++ Growth | +++ Growth | +++ Growth |

From this experimentation, it may be clearly seen that both tetrahydroiso-alpha acids and hexahydro-beta acids have strong antimicrobial or antibacterial properties, and are candidates for use in any application where they might be useful to combat *Staphylococcus aureus*, the primary causative agent in toxic shock syndrome.

For the purpose of applying these agents to combat toxic shock syndrome in infants, it was determined that directly incorporating them into the fabric of the diaper, or into the liquid present in a wet wipe to be used for cleansing of the infant, offered the greatest advantages. Various methods are known in the art for the application of liquid compositions to absorbent fabrics, and such methods are not considered as part of the present invention. Similarly, the addition of various components to the cleansing agents used in wet wipes is well known in the art, and not considered part of the present invention. Rather, the present invention is related to the selection of the specific antimicrobial compositions used, i.e. the tetrahydroiso-alpha acids and hexahydro-beta acids, provided that sufficient of the composition is provided so as to be an effective antimicrobial composition when in contact with a site subject to microbial growth. The specified compositions are readily available as by-products of the brewing industry, at relatively low cost. Being products of naturally occurring compositions, these acids are biodegradable, and safe for human usage, particularly as envisioned.

For application to a disposable diaper, it is proposed that a suitable mixture incorporating an effective concentration of the tetrahydroiso-alpha acid, hexahydro-beta acid, or a mixture thereof, be applied to a woven or non-woven cellulose-containing substrate, such as a moisture absorbent fabric of the type commonly used for diapers. Such fabrics are well known in the art, and any suitable such material may be used, including those containing super absorbent materials. It is also possible, although less advantageous, to include the antimicrobial composition of the invention in conventional cotton or other fabric diapers suitable for washing and re-use, although the antimicrobial composition will be removed from the fabric during normal washing.

The tetrahydroiso-alpha and hexahydro-beta acids employed are known to be soluble in water. Alternatively, they are also soluble in such materials as ethanol (and other alcohols), propylene glycol, glycerine, and polyols, or mixtures thereof with or without water. Such materials are quite suitable for, and are frequently employed in, diapers and wet wipes. Since the compounds are poorly soluble in plain water, alcohols are frequently used to prepare a solution. When water is used, it may be adjusted to a mildly alkaline pH to increase the solubility of the compounds.

The hop acid antimicrobials may be incorporated into the absorbent fabric, such as a disposable diaper, in conventional fashion, such as by passage of the fabric from a supply roll, into a pad bath containing an appropriate concentration of the antimicrobial in solution, through a nip roll to remove excess liquid, and into a dryer to dry the fabric to the touch, at temperatures adequate to remove excess water and other carriers without causing deterioration or conversion of the hop acid to an ineffectual form. To achieve a suitable disposable diaper in accordance with the invention, the diaper, after drying, and as packaged for consumer purchase, should have a sufficient amount of antimicrobial impregnated therein to be effective in combating *Staphylococcus aureus*. Such surface concentration may be achieved by passage of the diaper web through a bath of antimicrobial in a water or water/glycerine bath, the concentration of the antimicrobial being such as to provide the desired effective amount thereof. Passage through the bath and nip rolls at a rate appropriate to achieve an overall wet pickup of about 100 weight percent, based upon the weight of the fabric, is preferred. The impregnated fabric is then subjected to drying by passage through a dryer, typically through a stack of steam cans maintained at a suitable temperature that drying of the fabric may occur between about 200° and about 2500° F. so as to dry the fabric quickly but without effecting antimicrobial activity of the compounds incorporated into the fabric. If the antimicrobial composition is applied as an alcohol solution, the drying temperature may be lowered. The dried, finished product is then led away from the dryer, rolled, cut to size, and stored, wrapped in plastic bags or the like.

The preparation of wet wipes in accordance with the invention may be similarly conducted, with the exception of the drying step. The wet wipe fabric may be any fabric conventionally used for this purpose, and the anti-microbial hop acid may preferably be incorporated in a suitable liquid, such as a glycerine or polyglycol solution, for impregnation into the wet wipe. The wipe should be passed through a bath of the liquid, and passed through a nip roll or other means to eliminate excess liquid, and then cut to the chosen size and packaged in a plastic container, bag, etc. The concentration of the antimicrobial hop acid should preferably exceed about 0.00002 to about 0.100 weight percent of the solution, so as to achieve an effective amount thereof in the wipe at the time of usage. As in the preparation of diapers, the concentration of the antimicrobial should be sufficient to provide an effective amount thereof at the point of usage.

Although the present invention has been described in considerable detail with reference to certain preferred embodiments, one skilled in the art will appreciate that the present invention can be practiced by other than the preferred embodiments, which have been presented for purposes of illustration and not of limitation. For example, alternative methods of incorporation of the antimicrobial materials in the diapers, or in alternative materials, such as dressings or bandages, may be envisioned.

Therefore, the scope of the appended claims should not be limited to the description of the preferred embodiments contained herein.

INDUSTRIAL APPLICABILITY

The diapers and wet wipes of this invention are easily prepared using conventional apparatus and processes, employing hop acid antimicrobial materials which are derived from brewing processes by known methods.

We claim:

1. A method for inhibiting the growth of *Staphylococcus aureus* and toxic shock syndrome toxin-1 in liquids in contact with infants, said method comprising the step of:

diapering the infant with a dry diaper comprising a moisture absorbent, dry surface layer incorporating an effective amount of an antimicrobial compound consisting of tetrahydroiso-alpha acids, wherein the effective amount inhibits the growth of *Staphylococcus aureus*, wherein the effective amount is 0.1 ppm to 100 ppm based on the liquids, and wherein the liquids are acidic.

2. The method of claim 1, wherein said diaper is a disposable diaper, and said method inhibits toxic stress syndrome.

3. The method of claim 2, wherein said compound is applied to the diaper dissolved in a liquid selected from the group consisting of water, alcohols, propylene glycol, glycerin, polyglycols, and mixtures thereof, and said diaper is subsequently dried so as to be dry to the touch.

4. A dry diaper comprising a moisture absorbent, dry surface layer incorporating an antimicrobial compound consisting of tetrahydroiso-alpha acids, said antimicrobial compound being effective against toxic shock syndrome, wherein said antimicrobial compound is present in sufficient quantity to inhibit the growth of *Staphylococcus aureus* in liquids with which it is in contact, wherein the quantity is 0.1 ppm to 100 ppm based on the liquids, and wherein the liquids are acidic.

* * * * *

UNITED STATES PATENT AND TRADEMARK OFFICE
CERTIFICATE OF CORRECTION

| | |
|---|---|
| PATENT NO. | : 7,105,177 B1 |
| APPLICATION NO. | : 09/693123 |
| DATED | : September 12, 2006 |
| INVENTOR(S) | : Michael C. Barney et al. |

It is certified that error appears in the above-identified patent and that said Letters Patent is hereby corrected as shown below:

Column 3, line 50, "bateria" should be -- bacteria --.

Column 6, line 50, "2500°" should be -- 250° --.

Signed and Sealed this

Twenty-third Day of January, 2007

JON W. DUDAS
*Director of the United States Patent and Trademark Office*